United States Patent [19]
Creighton

[11] 3,959,353
[45] May 25, 1976

[54] ESTERS OF HYDROXYARYL ADDUCTS OF DECACHLOROPENTACYCLO (5.3.0.0$^{2,6}$.0$^{4,10}$0$^{5,9}$) DECANE-3-ONE

[75] Inventor: Stephen M. Creighton, Edmonton, Canada

[73] Assignee: Hooker Chemicals & Plastics Corporation, Niagara Falls, N.Y.

[22] Filed: May 29, 1973

[21] Appl. No.: 364,561

Related U.S. Application Data

[60] Division of Ser. No. 64,089, July 28, 1970, Pat. No. 3,816,543, which is a continuation of Ser. No. 592,719, Nov. 8, 1966, abandoned, which is a continuation-in-part of Ser. No. 191,703, May 2, 1962, abandoned.

[52] U.S. Cl. .......................... 260/479 R; 260/469; 260/476 C; 260/468 R
[51] Int. Cl.$^2$ .................. C07C 69/02; C07C 69/54
[58] Field of Search ..... 260/479 R, 488 CD, 476 C, 260/469, 468 R

[56] References Cited
UNITED STATES PATENTS

| | | | |
|---|---|---|---|
| 3,148,220 | 9/1964 | England | 260/613 |
| 3,185,736 | 5/1965 | Ellingboe | 260/619 |

OTHER PUBLICATIONS

Weygand, Preparative Organic Chem., (1972), pp. 879–881.

Kecher et al., Chem. Abstracts, vol. 79, (1973), p. 416.

*Primary Examiner*—James A. Patten
*Attorney, Agent, or Firm*—Peter F. Casella; James F. Mudd

[57] ABSTRACT

This invention relates to novel hydroxy-aromatic derivatives of decachloropentacyclo (5.3.0.0$^{2,6}$.0$^{4,10}$.0$^{5,9}$) decane-3-one ($C_{10}Cl_{10}O$) and to reaction products of such derivatives with carboxylic compounds; products of this invention are useful as resin intermediates in the preparation of unsaturated polyesters, and saturated polyesters which can be reacted with formaldehyde, trioxane, or hexamethylene tetramine to produce thermosetting plastics.

10 Claims, No Drawings

ESTERS OF HYDROXYARYL ADDUCTS OF DECACHLOROPENTACYCLO (5.3.0.0$^{2,6}$.0$^{4,10}$.0$^{5,9}$) DECANE-3-ONE

This is a division of application Ser. No. 64,089, filed July 28, 1970, now U.S. Pat. No. 3,816,543, which in turn is a continuation of application Ser. No. 592,719, filed Nov. 8, 1966, now abandoned, which is a continuation-in-part of application Ser. No. 191,703, filed May 2, 1962, now abandoned.

The present invention is concerned with new compositions of matter and to processes for their production.

More specifically, this invention relates to hydroxyaromatic derivatives of decachloropentacyclo(5.3.0.0.0$^{2,6}$.0$^{4,10}$.0$^{5,9}$) decane-3-one (C$_{10}$Cl$_{10}$O), methods for their production, and to reaction products of such derivatives with carboxylic compounds.

The products of this invention are useful as resin intermediates in the preparation of unsaturated polyesters, and saturated polyesters which can be reacted with formaldehyde, trioxane, or hexamethylene tetramine to produce thermosetting plastics. Also, by reacting the hydroxyaromatic compounds of the instant invention with an unsaturated aliphatic acid such as methacrylic, acrylic or their acid chlorides, unsaturated esters are produced which can be transformed to plastic materials by reaction of said esters with free radical generating catalysts such as benzoyl peroxide, methyl ethyl ketone peroxide, and the like.

The compounds of this invention also find utility as cross-linking agents for vinyl monomers, from which thermosetting plastics can be produced with enhanced thermal properties and fire resistance. In addition, the compounds of the instant invention are useful as additives to conventional polyesters derived from phthalic and maleic acid-diol systems.

It is an object of this invention to produce aromatic derivatives of decachloropentacyclo(5.3.0.0$^{2,6}$.0$^{4,10}$.0$^{5,9}$) decane-3-one.

Still another object of this invention is to utilize such aromatic derivatives in the preparation of novel intermediates for use in polymer manufacturing.

A further object is the production of carboxylic acid derivatives of the aromatic derivatives of decachloropentacyclo (5.3.0.0$^{2,6}$.0$^{4,10}$.0$^{5,9}$) decane-3-one.

These and other objects of the present invention will become more obvious from a consideration of the following detailed specification.

Decachloropentacyclo(5.3.0.0$^{2,6}$.0$^{4,10}$.0$^{5,9}$) decane-3-one, formerly known as decachlorotetrahydro-4,7-methanoindeneone, has the formula C$_{10}$Cl$_{10}$O and possesses the box ketone structure as follows:

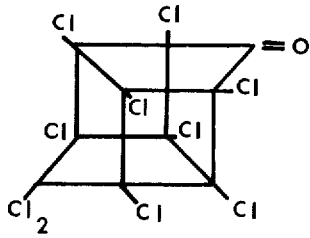

The aromatic derivatives of the present invention can be prepared by reacting an aromatic hydroxyl compound having at least one ortho or para position available for reaction, with decachloropentacyclo(5.3.0.0$^{2,6}$.0$^{4,10}$.0$^{5,9}$) decane-3-one in the presence of a suitable catalyst. The para positioned reaction product normally is of a higher melting point than the corresponding ortho product. The temperature is preferably in the range between about 50° centigrade and 200° centigrade, although higher and lower temperatures can be used such as about 0° centigrade to 225° centigrade. The reaction is usually complete in a period of between about one hour and about three hours. The aromatic hydroxyl compound functions as a solvent as well as a reactant in the process.

The compositions of this invention are presumably prepared by the following equation, although I do not wish to be limited by theory:

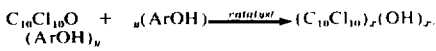

wherein $x$ is an integer of 1 to 30, and more preferably 1 to about 6, $y$ is an integer from 1 to 30, and more preferably 1 to about 6, and $z$ is an integer from 1 to 6.

The composition of the present invention is represented by the formula:

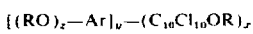

wherein $x$ is an integer of 1 to about 6, $y$ is an integer of 1 to about 6, $z$ is an integer of 1 to 6, Ar is aryl of 6 to about 24 carbon atoms and R is independently selected from the group consisting of hydrogen and acyl of 1 to about 10 carbon atoms. Ar is aryl or substituted aryl. Substituents on the aromatic ring may be H, F, Cl, Br or a suitable substituent selected from the following:

a. Alkyl groups of 1 to 18 carbon atoms in any of their isomeric forms and substituted on the phenolic nucleus in the ortho, meta or para positions;

b. Alicyclic groups of 5 to 18 carbon atoms such as cyclohexyl, cyclopentyl, methylcyclohexyl, butylcyclohexyl, and the like;

c. Aromatic or aralkyl groups of 6 to 18 carbon atoms such as phenyl, alpha-methyl-benzyl, benzyl, cumyl, and the like;

d. Alkyl, alicyclic, aryl and aralkyl ketones wherein the hydrocarbon is as described hereinbefore;

e. Alkyl, alicyclic, aryl and aralkyl carboxylic groups wherein the hydrocarbon is as described hereinbefore;

f. Alkyl, alicyclic, aryl and aralkyl ethers wherein the hydrocarbon is as described hereinbefore.

The substituents on the aromatic ring, including the hydroxyl groups, are bound to the aromatic ring system Ar, which may be a single ring such as benzene and the like, or a plurality of benzene rings linked together directly or by oxygen, carbon, sulfur, phosphorus, alkyl as defined above, or a fused aromatic ring system such as naphthalene, phenanthrene, and the like.

Suitable substituted phenols include the following: para-tertiary-butylphenol, para-secondary-butylphenol, para-tertiary-hexylphenol, para-isooctylphenol, para-phenylphenol, para-benzylphenol, para-cyclohexylphenol, para-decylphenol, para-dodecylphenol, para-tetradecylphenol, para-octadecylphenol, para-nonylphenol, para-methylphenol, para-beta-naphthylphenol, para-alpha-naphthylphenol, para-pentadecylphenol, para-cetylphenol, para-cumylphenol, para-hydroxy acetophenone, para-hydroxy benzophenone, a phenol alkylated with limonene, a phenol alkylated with oleic acid, as well as the corresponding ortho and meta derivatives such as meta-butylphenol and ortho-butylphenol, as well as mixtures thereof.

Other hydroxyl aromatics which may be used in preparing the compositions of the instant invention are phenol-aldehyde condensation products which are fusible and soluble such as novolaks or resoles, bisphenols, resorcinol, catechol, hydroquinone, phloroglucinol, polyhydroxynaphthalenes and such compounds containing substituents such as defined for the substituents on the aromatic ring hereinbefore. Novolak refers to a compound formed by the condensation of a phenol with an aldehyde in the presence of a catalyst and an acid, while a resole refers to the reaction between a phenol and an aldehyde in the presence of a base. The novolak is prepared by reacting about 0.5 to 1 mole of aldehyde per mole of phenol, while a resole requires more than one mole of aldehyde per mole of phenol.

Illustrative bisphenols include:
4,4-dihydroxy-diphenyl methane
4,4-dihydroxy-diphenyl-1,1-ethane
4,4-dihydroxy-diphenyl-1,1-n-butane
4,4-dihydroxy-diphenyl-1,1-heptane
4,4-dihydroxy-diphenyl-phenyl-methane
4,4-dihydroxy-diphenyl-2,2-propane
4,4-dihydroxy-3,3-dimethyl-diphenyl-2,2-propane
4,4-dihydroxy-3,3-diphenyl-diphenyl-2,2-propane
4,4-dihydroxy-3,3-dichlor-diphenyl-2,2-propane
4,4-dihydroxy-diphenyl-2,2-butane
4,4-dihydroxy-diphenyl-2,2-pentane
4,4-dihydroxy-diphenyl-methyl-isobutyl-methane
4,4-dihydroxy-diphenyl-2,2-heptane
4,4-dihydroxy-diphenyl-2,2-octane
4,4-dihydroxy-diphenyl-3,3-pentane
4,4-dihydroxy-diphenyl-4,4-n-heptane
4,4-dihydroxy-diphenyl-1,1-cyclopentane
4,4-dihydroxy-diphenyl-1,1-cyclohexane
4,4-dihydroxy-diphenyl-methyl-phenyl-methane
4,4-dihydroxy-diphenyl-ethyl-phenyl-methane
4,4-dihydroxy-diphenyl-(2,2,2-trichlor)-1,1-ethane Typical compounds prepared by this invention are as follows:

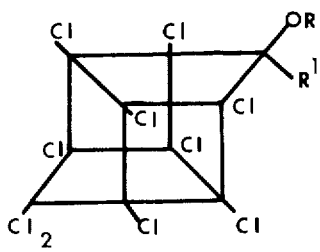

where $R^1$ is:

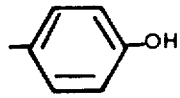

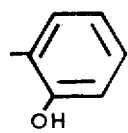

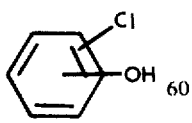

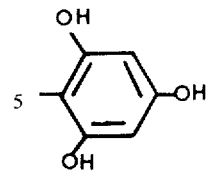

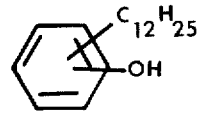

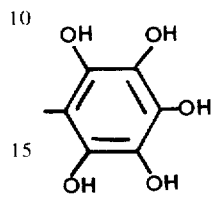

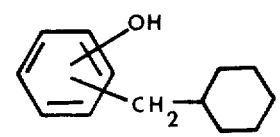

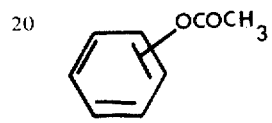

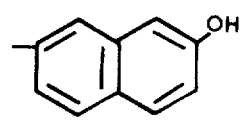

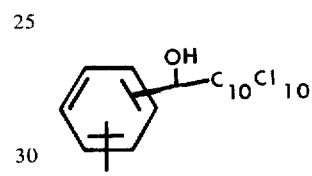

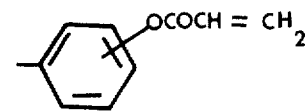

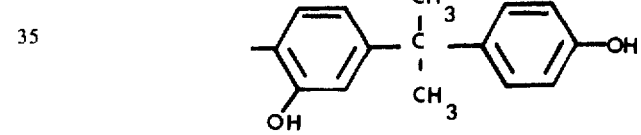

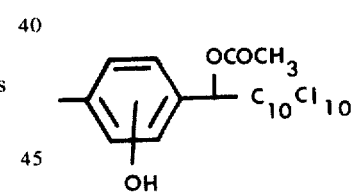

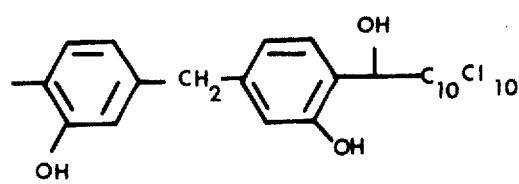

and the like and R is:
hydrogen
—COCH$_3$
—COC$_2$H$_5$
—COCCH=CH$_2$
—COC$_6$H$_{13}$
—COCH=CHCOOH
and the like. The group R may be the same as or different from the acyl group on the substituent R' when R' contains an acyl group.

Compounds such as

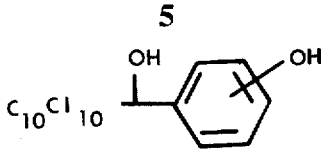

can be further reacted to produce the bisphenols and derivatives thereof, such as

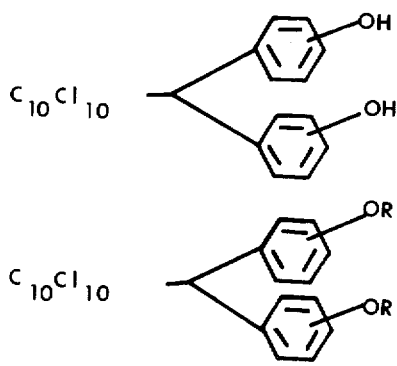

wherein R is as described above.

In accordance with the present invention as carboxylic acid derivatives of the aromatic derivatives of decachloropentacyclo $(5.3.0.0^{2,6}.0^{4,10}.0^{5,9})$decane-3-one can be prepared. A temperature from about 75° centigrade to about 200° centigrade is employed, and a catalyst may or may not be utilized in the preparation of these derivatives. Further, any convenient pressure which includes atmospheric, subatmospheric or superatmospheric may be employed.

The carboxylic compound employed herein refers to a mono or polycarboxylic commpound which can either be saturated or unsaturated. Such compounds include the acids, acid halides and add esters, wherein the acid is of 1 to about 10 carbon atoms. Examples of the mono carboxylic compounds are acetic, propionic, benzoic, toluic, acrylic, methacrylic and the like. Suitable unsaturated polycarboxlic acids and the corresponding acid halides, esters, anhydrides, and acid esters can include maleic, chloromaleic, ethylmaleic, itaconic, citraconic, zeronic, pyrocinchoninic and acetylene dicarboxylic, either alone or in mixtures.

The saturated polycarboxylic compounds useful in the invention ca be aliphatic, cycloaliphatic, aromatic or heterocyclic of 2 to about 10 carbon atoms. Illustrative of these polycarboxylic acids, acid halides, acid anhydrides and acid esters include phthalic, isophthalic, terephthalic, tetrachlorophthalic, adipic, succinic, 3,4,5,7,7-hexachloro(1.2.2)-bicycloheptene-1,2-dicarboxylic acid (Hot Acid) and mixtures thereof.

The following specific examples further illustrate the invention. However, this detailed disclosure is not to be construed as limiting the scope of the present invention.

EXAMPLE 1

Preparation of the α-isomer of 3-Hydroxy-3-(hydroxyphenyll-decachloropentacyclo $(5.3.0.0^{2,6}.0^{4,10}.0^{5,9})$-decane $(C_{16}H_6Cl_{10}O_2)$.

In a three-necked flask there was placed 92.1 grams of decachloropentecyclo-$(5.3.0.0^{2,6}.0^{4,10}.0^{5,9})$decane-3-one, 20.0 grams of phosphorus pentoxide, and 70.5 grams of phenol. The mixture was heated at 100° centigrade which resulted in a fluid translucent mass which was then cooled to 70° centigrade and HCl gas was passed with good agitation. The exothermic reaction carried the temperature up to 90° centigrade, and the reaction mixture gradually solidified. Heat was applied to maintain the temperature at 90° centigrade and the reaction was allowed to proceed for three hours. It became too solid to stir, was steam distilled, and the crystalline material that was present in the distillant was filtered off. A portion of this material was recrystallized from aqueous methanol, then from toluene. The final product was a white crystalline material of melting point 266.5 - 268.5 degrees centigrade (uncorrected) and contained 60.5 per cent chlorine. Calculated chlorine content for $C_{16}H_8Cl_{10}O_2$ is 60.63 per cent. The product was established to be the α isomer of 3-hydroxy-3-(hydroxyphenyl)-decachloropentacyclo $(5.3.0.0^{2,6}.0^{4,10}.0^{5,9})$decane.

EXAMPLE 2

Conversion of the α-isomer of 3-hydroxy-3-(hydroxyphenyl)-decachloropentacyclo $(5.3.0.0^{2,6}.0^{4,10}.0^{5,9})$decane to the diacetate $(C_{20}H_{10}Cl_{10}O_4)$ Two grams of the α-isomer was dissolved in 20 ml of pyridine and 9 ml of acetic anhydride was added slowly. The reaction mixture was refluxed for 1 hour, cooled to 0° centigrade and then poured into ice water and the resulting precipitate was removed on a filter and dried (m.p. 164° centigrade uncorrected). The dried precipitate was washed at reflux with methanol and dried (m.p. 169°–170° centigrade uncorrected). After a recrystallization from alcohol, a white crystalline product was obtained which had a melting point of 170°– 171.5° centigrade and was found to contain 52.7 per cent chlorine. The calculated chlorine content for the diacetate of the α-isomer $(C_{10}H_{10}Cl_{10}O_4)$ is 53.0 per cent. The product was established to be the diacetate of the α-isomer of 3-hydroxy-3-(hydroxyphenyl)-decachloropentacyclo $(4.3.0.0^{2,6}.0^{4,10}.0^{5,9})$-decane.

The compound resulting from the above reaction is suitable for use as a fire-retardant additive in plastic materials.

EXAMPLE 3

Preparation of the monomethacrylate of the α-isomer of 3-hydroxy-3(hydroxyphenyl)-decachloropentacyclo $(5.3.0.0^{2,6}.0^{4,10}.0^{5,9})$-decane α-isomer (87.5 grams) was dissolved in 200 milliliters of pyridine with a slight evolution of heat. Methacrylyl chloride (47.1 grams) was added dropwise causing a white solid to precipitate due to an exothermic reaction. After the addition of the acid chloride, the heterogeneous reaction mixture was heated to 115° centigrade, and allowed to cool to 90° centigrade at which temperature it was maintained for 1.5 hours. After standing over the weekend, one liter of 10 per cent HCl was added and the solid material was removed on a filter and washed with water. After drying, the product was extracted with benzene, the benzene layer was washed with water, decolorized with carbon, and concentrated. The crystalline material was removed on a filter and recrystallized from benzene. The final product had a melting point of 222°–223° centigrade (uncorrected) and was found to contain 56.2 per cent chlorine. The chlorine content calculated for the monomethacrylate of the α-isomer $(C_{20}H_{10}O_3Cl_{10})$ is 54.3 per cent. The product was established to be the monomethacrylate of the α-isomer of 3-hydroxy-3-(hydroxyphenyl)-decachloropentacyclo $(5.3.0.0^{2,6}.0^{4,10}.0^{5,9})$-decane.

The resulting unsaturated ester produced in this example is readily transformed to a plastic material by the addition of a free radical generating catalyst such as benzoyl peroxides, etc.

EXAMPLE 4

Preparation of the β-isomer ($C_{16}H_6Cl_{10}O_2$) of 3-hydroxy-3 (hydroxy phenyl) decachloropentacyclo $(5.3.0^{2,6}.0^{4,10}.0^{5,9})$decane In a three-necked flask there was placed 118.5 grams of the hydrate of decachloropentacyclo- $(5.3.0.0^{2,6}.0^{4,10}.0^{5,9})$-decane-3-one and 49.0 grams of phenol and heated to 150° centigrade to effect solution. The solution was cooled to 86° and 35.0 grams of $AlCl_3$ were added slowly in small portions. The reaction mixture slowly turned to a deep blue hard mass. Water (one liter) was slowly added to the reaction mixture, and a blue gray powder resulted. After the addition of water, 200 milliliters of concentrated HCl was added. Some evolution of gas took place and a slate gray precipitate resulted, which was washed free of acid with water. After drying, there was obtained 123 grams of product melting 222°–229° centigrade.

Recrystallization from 75 per cent aqueous methanol, followed by a recrystallization from methanol afforded a product which had a melting point of 249° – 250° centigrade (uncorrected) and a chlorine content of 61.2 per cent. The calculated for formula weight for $C_{16}H_6Cl_{10}O_2$ is 584.8 and the chlorine content 60.6 per cent. The product was established to be the β isomer of 3-hydroxy-3(hydroxy phenyl) decachloropentacyclo $(5.3.0.0^{2,6}.0^{4,10}.0^{5,9})$ decane.

EXAMPLE 5

Conversion of the β-isomer of Example 4 to the diacetate ($C_{20}H_{10}Cl_{10}O_4$)

The quantities of reagents and procedure for the preparation of the diacetate of the β-isomer were identical to those used for the α-isomer described above. The diacetate of the β-isomer is a crystalline product which melted at 223.0° – 233.5° centigrade (uncorrected) and contained 53.2 per cent chlorine. Calculated chlorine content for $C_{20}H_{10}Cl_{10}O_4$ is 53.0 per cent.

EXAMPLE 6

Preparation of the dimethacrylate of the β-isomer of 3-hydroxy-3-(hydroxyphenyl)-decachloropentacyclo $(5.3.0.0^{2,6}.0^{4,10}.0^{5,9})$ decane The quantities of the reagents and the procedure used for the preparation of the dimethacrylate of the β-isomer was the same as that used for the preparation of the monomethacrylate of the α-isomer described above. In the final work-up the dimethacrylate of the β-isomer was recrystallized twice from benzene-heptane and finally benzene. The crystalline product thus obtained melted at 199° – 200° centigrade (uncorrected) and the melt rapidly polymerized to a gel at the melting point. It was found to contain 49.5 per cent chlorine. The calculated chlorine content for the dimethacrylate of the β-isomer ($C_{24}H_4Cl_{10}O_4$) is 49.2 per cent. The product was established to be the dimethacrylate of the β-isomer of 3-hydroxy-3-(hydroxyphenyl)-decachloropentacyclo $(5.3.0.0^{2,6}.0^{4,10}.0^{5,9})$ decane.

Although the above examples and descriptions of this invention has been very specifically illustrated, many other modifications will suggest themselves to those skilled in the art upon a reading of this disclosure. These are intended to be comprehended within the scope of this invention.

I claim:

1. A compound of the formula

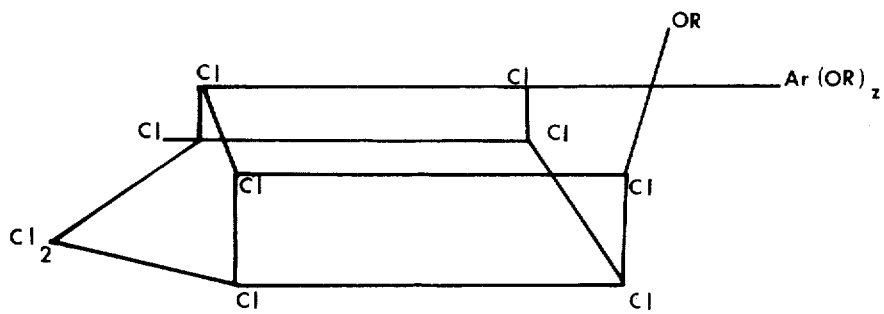

wherein z is an integer of 1 to 6; R is independently selected from the group consisting of hydrogen and hydrocarbyl acyl of 1 to 10 carbon atoms, provided that at least one R is hydrocarbyl acyl; and Ar is selected from the group consisting of phenyl, naphthyl, and substituted aryl of from 6 to 24 carbon atoms, wherein said aryl nucleus is phenyl or naphthyl and said substituents are independently selected from the group consisting of a. alkyl of 1 to 18 carbon atoms;
b. cyclohexyl or cyclopentyl;
c. hydrocarbyl aralkyl of 7 to 18 carbon atoms; and
d. a halogen independently selected from the group consisting of fluorine, chlorine or bromine.

2. A compound of the formula

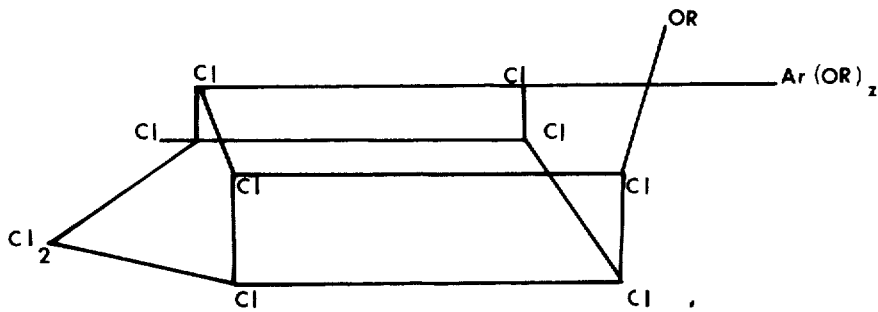

wherein z is an integer of 1 to 6, R is independently selected from the group consisting of hydrogen and hydrocarbyl acyl of 1 to 10 carbon atoms, provided that at least one R is hydrocarbyl acyl; and Ar is selected from the group consisting of aryl of 6 to 24 carbon atoms, and substituted aryl of 6 to 24 carbon atoms wherein the substituents thereon are selected from the group consisting of:

a. alkyl groups of 1 to 18 carbon atoms;
b. cyclopentyl or cyclohexyl;
c. alkyl of 1 to 8 carbon atoms substituted by a group selected from a group consisting of cyclopentyl, cyclohexyl, phenyl, hydroxy phenyl, up to 3 chlorine atoms, a disubstitution of phenyl and hydroxy phenyl, a trisubstitution of dichloro and hydroxy phenyl, and a tetrasubstitution of three chlorine atoms and a hydroxy phenyl;
d. cyclopentyl or cyclohexyl substituted by hydroxy phenyl;
e. phenyl or naphthyl;
f. lower alkyl ketone or phenyl ketone;
g. a halogen selected from the group consisting of fluorine, chlorine and bromine.

3. The compound of claim 1 which is the diacetate of the α isomer of 3-hydroxy-3-(hydroxyphenyl)-decachloropentacyclo $(5.3.0.0^{2,6}.0^{4,10}.0^{5,9})$ decane.

4. The compound of claim 2 which is the monomethacrylate of the α isomer of 3-hydroxy-3-(hydroxyphenyl)-decachloropentacyclo $(5.3.0.0^{2,6}.0^{4,10}.0^{5,9})$ decane.

5. The compound of claim 2 which is the diacetate of the β isomer of 3-hydroxy-3-(hydroxyphenyl)-decachloropentacyclo $(5.3.0.0^{2,6}.0^{4,10}.0^{5,9})$ decane.

6. The compound of claim 2 which is the dimethacrylate of the β isomer of 3-hydroxy-3-(hydroxyphenyl)-decachloropentacyclo $(5.3.0.0^{2,6}.0^{4,10}.0^{5,9})$ decane.

7. The compound of claim 1 wherein z is 1.

8. The compound of claim 1 wherein z is 3.

9. The compound of claim 1 wherein Ar is substituted phenyl, wherein the substituent is hydrocarbyl aralkyl of 7 to 18 carbon atoms.

10. The compound of claim 1 wherein both R groups are hydrocarbyl acyl.

* * * * *